United States Patent [19]
Funk et al.

[11] Patent Number: 5,618,972
[45] Date of Patent: Apr. 8, 1997

[54] PROCESS FOR CONTINUOUS REACTION AND SEPARATION USING FIXED CATALYST BED SERIALLY CONNECTED TO SIMULATED MOVING CATALYST AND ADSORBENT BED

[75] Inventors: Gregory A. Funk, Carol Stream; Hemant W. Dandekar; Simon H. Hobbs, both of Chicago, all of Ill.

[73] Assignee: UOP, Des Plaines, Ill.

[21] Appl. No.: 394,995

[22] Filed: Feb. 27, 1995

[51] Int. Cl.$^6$ .................................................. C07C 67/08
[52] U.S. Cl. ................................................................ 560/239
[58] Field of Search ............................................... 560/239

[56] References Cited

U.S. PATENT DOCUMENTS

| | | | |
|---|---|---|---|
| 3,864,240 | 2/1975 | Stone | 208/64 |
| 4,008,291 | 2/1977 | Zabransky et al. | 260/683.43 |
| 4,028,430 | 6/1977 | Stine et al. | 260/683.43 |
| 4,049,739 | 9/1977 | Zabransky et al. | 260/671 R |
| 4,072,729 | 2/1978 | Stine et al. | 260/671 R |
| 4,435,595 | 3/1984 | Agreda et al. | 560/234 |
| 5,113,024 | 5/1992 | Harandi et al. | 568/697 |
| 5,190,639 | 3/1993 | Swart et al. | 208/65 |
| 5,211,838 | 5/1993 | Staubs et al. | 208/65 |
| 5,354,451 | 10/1994 | Goldstein et al. | 208/65 |
| 5,405,992 | 4/1995 | Funk et al. | 560/265 |
| 5,530,172 | 6/1996 | Funk et al. | 585/736 |
| 5,530,173 | 6/1996 | Funk et al. | 585/737 |

FOREIGN PATENT DOCUMENTS

WO9207097  4/1992  WIPO ........................... C13K 3/00

*Primary Examiner*—Gary Geist
*Assistant Examiner*—Rosalynd Williams
*Attorney, Agent, or Firm*—Thomas K. McBride; Eugene I. Snyder; Maryann Maas

[57] ABSTRACT

A two-stage process for effecting a chemical reaction has been developed. The reactants are contacted with a first stage fixed catalyst bed containing a solid catalyst or mixture of catalysts effective to catalyze the reaction and form a mixture of reactants and products. This reaction mixture and a desorbent are then contacted with a second stage simulated moving bed containing a solid or a mixture of solids effective to catalyze the reaction and to selectively adsorb at least one component from the reaction mixture. At least one product-containing stream is formed and collected. The process may be conducted in the liquid phase or in the vapor phase.

26 Claims, 1 Drawing Sheet

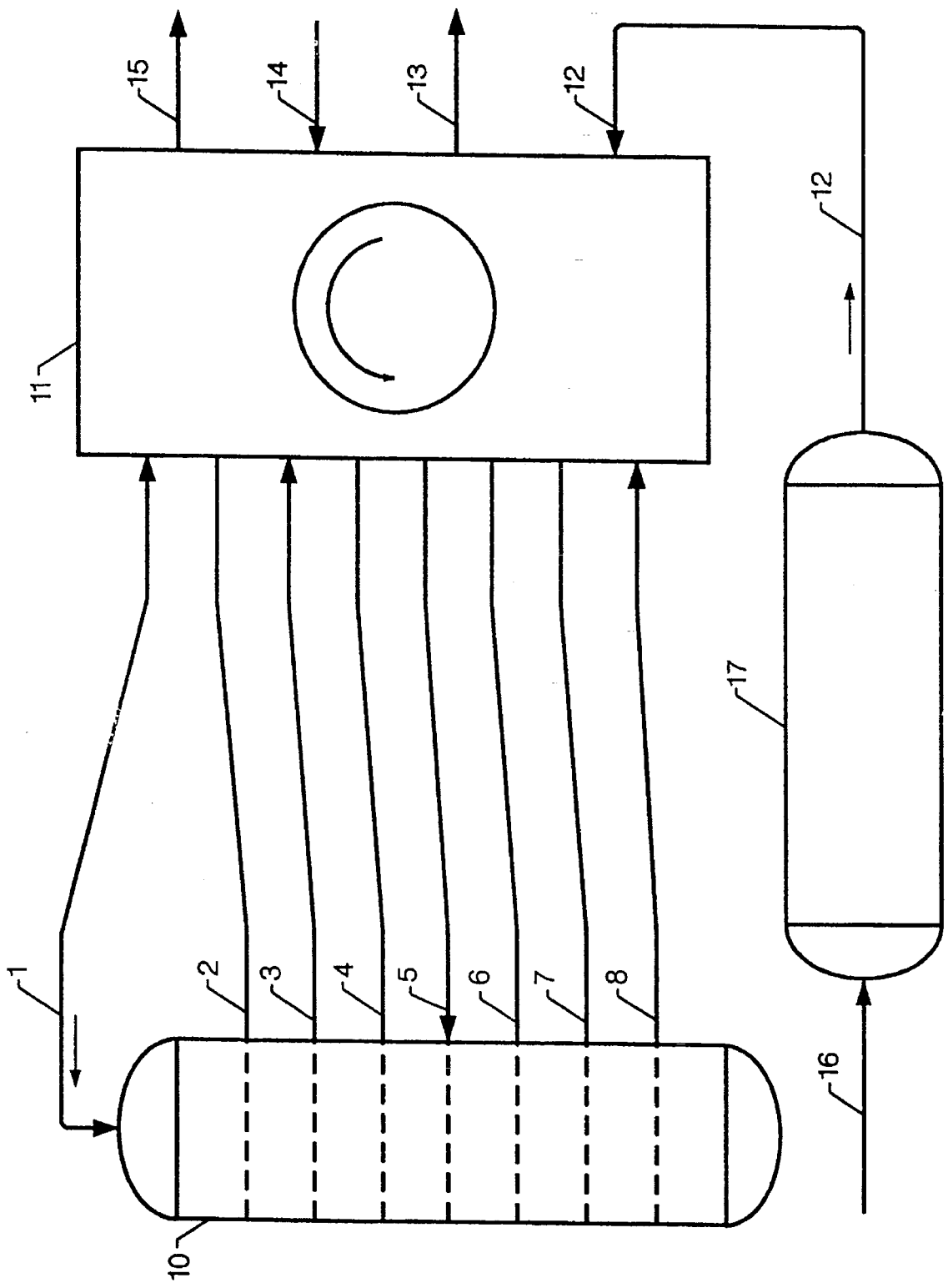

PROCESS FOR CONTINUOUS REACTION AND SEPARATION USING FIXED CATALYST BED SERIALLY CONNECTED TO SIMULATED MOVING CATALYST AND ADSORBENT BED

BACKGROUND OF THE INVENTION

Many chemical reactions are equilibrium limited. When chemical equilibrium is reached, the rate of forward reaction equals the rate of the reverse reaction, thus imposing a limit on the degree to which reactants can be converted to products. Therefore, the chemical equilibrium acts to limit the efficiency of the reaction. Although the amount of product available from an equilibrium-limited reaction is restricted, the products formed may be sufficiently valuable for one to attempt the reaction in spite of the limitation. Industry has used several techniques to maximize the amount of product formed. For example, the most common approach has been to further process a fixed bed reactor effluent containing an equilibrium mixture of reactants and products in order to separate the products from the reactants and recycle the reactants to the fixed bed reactor. The separated product may be collected, and recycling the reactants avoids waste. However, when using this approach, the reactant recycle volume is often large and costly, and appreciable amounts of reactants may be needed to form relatively small amounts of product. An example of using a reactor in series with separation techniques and recycling unconverted reactants may be found in U.S. Pat. No. 5,113,024, where diisopropyl ether is formed from water and propylene. This patent teaches that unconverted propylene in the reactor effluent may be separated from the product and byproducts by extraction and recycled to the reactor.

Another approach has been to make use of the knowledge that the separation of one or more products from the reaction mixture will upset the chemical equilibrium and allow additional product formation. Reactive distillation is a common example of this approach. With reactive distillation, the reaction is conducted under distillation conditions so that as product is being formed, it is rapidly separated from the reactants by distillation, thereby shifting equilibria to favor the yield of products. The reaction of methanol and acetic acid to form methyl acetate has been carried out using this technique; see U.S. Pat. No. 4,435,595.

This same reaction has been disclosed in U.S. Pat. No. 5,405,992 as being conducted by reactive chromatography which similarly separates the reaction products from each other in order to shift equilibria to favor the yield of products. A general discussion of reactive chromatography may be found in, Vaporciyan, G. G.; Kadlec, R. H. *AIChE J.* 1987, 33 (8), 1334–1343; Fish, B. B.; Carr, R. W. *Chem. Eng. Sci.* 1989, 44, 1773–1783; and Carr, R. W. In *Preparative and Production Scale Chromatography;* Ganetsos, G., Barker, P. E., Eds.; Chromatographic Science Series Vol. 61; Marcel Dekker: New York, 1993; Chapter 18. U.S. Pat. No. 5,405,992 teaches using a simulated moving bed containing a solid or mixture of solids that is effective both to catalyze an esterification reaction of an alcohol and a carboxylic acid, and to separate the products from each other through adsorption of at least one product in order to increase the yield of a product ester. Simulated moving bed reactive chromatography units may require substantial capital investment, and the present invention maintains the equilibria shift to favor the yield of products as provided by reactive chromatography, but allows the size of the simulated moving bed reactive chromatography unit to be substantially reduced, thereby reducing the capital investment. The present invention operates with a fixed bed of catalyst serially connected to a simulated moving bed reactive chromatography unit. In the fixed bed of catalyst, the reaction proceeds to partial completion or, in a preferred embodiment, until chemical equilibrium is reached. The reaction mixture is passed to the simulated moving bed reactive chromatography unit where the products are separated from the reactants causing additional product formation.

Fixed catalyst beds have been combined with other types of catalyst beds such as in U.S. Pat. Nos. 5,354,451, 5,211,838, 5,190,639, and 3,864,240 where a fixed catalyst bed or multiple fixed catalyst beds are used with a moving catalyst bed to perform catalytic reforming. Fixed catalyst beds have also been combined with simulated moving adsorbent beds, as in WO 92/07097 where a fixed catalyst bed, used to produce glucose and fructose from sucrose, is combined with a simulated moving bed to separate the glucose and fructose. However, applicants are the first to realize that a fixed catalyst bed and a simulated moving bed reactive chromatography unit can be successfully combined to improve the effectiveness of the fixed catalyst bed and to improve the cost efficiency of the simulated moving bed reactive chromatography unit.

The two-stage approach of the present invention provides enhancements over both a single stage fixed bed process and a single stage simulated moving bed process. For example, in the two-stage process of the invention, performing a portion of the reaction in a fixed catalyst bed reduces the size of the simulated moving bed as compared to the size needed where the entire reaction takes place in a simulated moving bed. Since fixed catalyst beds are less expensive to build, operate, and maintain than more sophisticated reactors such as moving bed or simulated moving bed reactors, the cost of the fixed bed is more than offset by the available savings through the reduction of the size of the simulated moving bed. Also, any catalyst poisons in the system will likely foul the catalyst in the fixed bed and not reach the catalyst in the simulated moving bed. Catalyst replacement or regeneration in a fixed bed is rudimentary compared to catalyst replacement or regeneration in a simulated moving bed. The simulated moving bed part of the combination provides the capacity to take the reaction largely to completion while due to equilibrium limitations the fixed catalyst bed alone would provide only partial reaction.

SUMMARY OF THE INVENTION

The purpose of the invention is to provide a two-stage continuous process for effecting a chemical reaction with concurrent separation of at least one of the products formed. The reactants are contacted with a first stage fixed catalyst bed containing a solid catalyst or a mixture of catalysts effective to catalyze the reaction and form a mixture of reactants and products. In a preferred embodiment, the reactant and product mixture will be at equilibrium. The mixture of reactants and products and a desorbent are then contacted with a second stage simulated moving bed containing a solid or a mixture of solids effective to catalyze the reaction and to selectively adsorb at least one component. At least one product-containing stream is formed and collected. The invention may be conducted in the liquid phase or in the vapor phase.

A specific embodiment of the invention is one where the catalyst contained in the fixed bed and the catalyst contained in the simulated moving bed are identical. Another specific embodiment of the invention is one where the second stage simulated moving bed mixture of solids contains a solid effective as a catalyst and a solid effective as an adsorbent present in a ratio of from about 1:50 to about 50:1. Still another specific embodiment is one where the second stage simulated moving bed contains a solid that is both effective as a catalyst and as an adsorbent. Yet another specific embodiment of the invention is one where substantially all of at least one reactant is consumed in the second stage.

BRIEF DESCRIPTION OF THE DRAWING

The Figure is a schematic representation of a generic commercial process using a fixed catalyst bed connected serially to a simulated moving bed, modified and operated in accordance with the process of this invention. The Figure has been simplified by the deletion of a large number of pieces of apparatus customarily employed on a process of this nature which are not specifically required to illustrate the performance of the subject invention.

DETAILED DESCRIPTION OF THE INVENTION

The invention is a process for effecting a continuous chemical reaction using a fixed catalyst bed serially connected with a simulated moving bed able to effect reactive chromatography, i.e., a process where a simulated moving bed both catalyzes the reaction and effects the separation of at least one component of the reaction mixture. In general terms, the reactants are contacted with a first stage fixed catalyst bed and then with a second stage simulated moving bed of a solid or a mixture of solids. The fixed catalyst bed is effective to catalyze the reaction and a portion of the reactants are converted to produce a reaction mixture containing reactants and products. This reaction mixture is then passed to the simulated moving bed which is effective both to catalyze the same reaction and to separate at least one component of the reaction mixture through selective adsorption. When a product is removed by selective adsorption, the equilibrium of the reaction is shifted and additional product formation occurs. The adsorbed product is then desorbed by a desorbent and recovered. When a reactant is removed by selective adsorption, the products may be removed from the system before the reverse reaction is able to occur. Through selective adsorption of the reactant, the residence time of the reactant in the system is increased in order to allow the forward reaction to continue.

Fixed catalyst bed, reactive chromatography, and simulated moving bed technologies are known in the art, and a general discussion of these technologies may be found in Kirk-Othmer, *Encyclopedia of Chemical Technology;* 3rd ed.; John Wiley & Sons: New York; Vol. 19, pp. 880–914 for the fixed catalyst bed; Mowry, J. R. In *Handbook of Petroleum Refining Processes;* Meyers, R. A. Ed.; McGraw-Hill: New York, 1986; pp. 8-79 to 8-99 for the simulated moving bed; and *Preparative and Production Scale Chromatography;* Ganetsos, G., Barker, P. E., Eds.; Chromatographic Science Series Vol. 61; Marcel Dekker: New York, 1993; Chapters 16–21 for reactive chromatography. Applicants have realized that these technologies may be effectively combined in a two-stage process and the details of the instant invention are supplied below.

The first stage of the invention uses a fixed catalyst bed which contains solids effective to catalyze the desired reaction. The specific catalyst used depends upon the particular reaction. One catalyst may be used or two or more catalysts may be combined in a homogeneous mixture and used in the fixed catalyst bed. The preferred mode of the invention is one where the first stage contains only one fixed catalyst bed. It is contemplated, however, that multiple fixed catalyst beds, or sub-beds, may be connected and used as the first stage of the process. The details of operating a fixed catalyst bed are well known in the art and are not discussed here.

The second stage of the invention uses a simulated moving bed which is made up of particles of a solid or a mixture of solids that together are effective to both catalyze the reaction and to perform the separation. Usually, two or more solids, at least one being a catalyst and at least one being an adsorbent, are used as a homogeneous mixture. However, it is also possible that one solid may perform both the catalyst function and the adsorbent function. The specific catalyst and adsorbent used in this invention will depend on the particular reaction desired. The catalyst must be present in an amount effective to catalyze the reaction. The catalyst in the fixed catalyst bed may be the same as, or may be different from, the catalyst in the simulated moving bed. The adsorbent in the simulated moving bed must be capable of adsorbing at least one reactant or at least one product and must be present in an amount effective to 1) adsorb at least enough of one product to shift the equilibrium to favor product formation, or 2) adsorb enough of one reactant so that products are formed. Also, depending upon the separation needed, several different adsorbents may be combined in order to accomplish the separation function. Different applications may require different ratios of catalyst to adsorbent or different catalyst and adsorbent combinations. For most applications, the catalyst to adsorbent ratio is usually in the range of about 1:50 to about 50:1. The details of operating a simulated moving bed are well known in the art and are not discussed here. An example may be found in U.S. Pat. No. 5,405,992.

The invention may be understood by illustrating the process as applied to a particular generic reaction, such as A$\rightleftharpoons$B+C. Reactant A is continuously introduced to a fixed catalyst bed containing a sufficient amount of catalyst effective to catalyze the reaction A$\rightleftharpoons$B+C. The reactants may be liquid or vapor, and the reactant may be present in a mixture with a fluid carrier which is in the same phase. The fixed catalyst bed is operated at conditions optimal to the reaction. As reactant A contacts the catalyst, the reaction occurs to form B and C. When chemical equilibrium is reached, the ratio of the concentrations of A, B and C remain constant, and no increase in the concentrations of B and C are accomplished. This equilibrium reaction mixture exits the fixed catalyst bed and is directed to the simulated moving bed which contains a homogeneous mixture of catalyst, which may be the same catalyst as used in the fixed catalyst bed, and an adsorbent which for this illustration selectively adsorbs product B. The simulated moving bed is operated at conditions suitable for the reaction and separation. As the equilibrium reaction mixture contacts the catalyst and adsorbent mixture, product B is selectively adsorbed and removed from the remaining concentrations of reactant A and product C via the simulated movement of the solids. With the removal of product B, the equilibrium of the reaction shifts to favor the formation of products, and as reactant A contacts the catalyst, additional amounts of products B and C are produced. As product B is formed, it is immediately selectively adsorbed by the adsorbent and removed, thereby maintaining the equilibrium in favor of producing products. The reaction continues, and product formation increases. With proper conditions, the reaction may continue until substantially all of reactant A is converted. For purposes of this invention, substantially refers to 90 percent or greater. Additionally, a desorbent capable of desorbing the selectively adsorbed product B from the adsorbent is introduced to the simulated moving bed providing a fluid flow in the countercurrent direction of the simulated movement of the solids. The selectively adsorbed product B is carried with the simulated movement of the solids to a point in the vicinity of where the desorbent is introduced. As the large concentration of desorbent contacts the solids, the product B is desorbed and may be removed from the simulated moving bed and recovered. Product C that was not adsorbed is simply carried with the fluid flow and removed from the simulated moving bed. Note that the two products are separated in this illustration. The process continues in this manner.

Numerous variations of this simple illustration will be apparent to one skilled in the art. For example, one would readily understand how an adsorbent may be chosen so that product C is selectively adsorbed instead of product B, or perhaps both may be adsorbed to varying degrees. One will also understand that the process is most valuable when applied to equilibrium-limited reactions, but that an equilibrium limitation is not a necessity. Similarly, one would understand that the desorbent may also be a reactant that is capable of desorbing the selectively adsorbed component.

In a specific variation where the reaction is $A \leftrightarrows B$, the adsorbent may be chosen so that reactant A is selectively adsorbed by the adsorbent instead of the product B. In this case, as the equilibrium reaction mixture from the fixed catalyst bed enters the simulated moving bed and contacts the adsorbent and catalyst mixture, reactant A is selectively adsorbed by the adsorbent. Product B is carried with the fluid flow, removed from the simulated moving bed before the reverse reaction occurs, and recovered. Reactant A is carried with the simulated movement of the solids countercurrently to the fluid flow. Reactant A is desorbed from the adsorbent by the incoming desorbent, contacts the catalyst, and additional amounts of product B is produced. The increased residence time of reactant A allows for a greater amount of product B formation, while the decreased residence time of product B minimizes the occurrence of the reverse reaction. The process continues in this manner.

From the foregoing illustrations, it is clear to one skilled in the art that the instant invention may also be applied to reactions such as $A+B \leftrightarrows C+D$, $A+B \leftrightarrows C$, and the like, so long as an adsorbent and a catalyst are available that have the capability of performing their respective functions at the operating conditions of the simulated moving bed. An example of a specific reaction which could be accomplished using the present invention is the continuous esterification of at least one alcohol and at least one carboxylic acid to produce at least one ester and water. An even more specific example is the reaction of methanol and acetic acid to form methyl acetate and water. In this specific situation, examples of suitable catalysts for use in both the fixed catalyst bed and the simulated moving bed include zeolite Beta, strongly acidic macroreticular polymeric resins and silicalite, and examples of suitable adsorbents include alumina, silica, molecular sieve carbon, activated carbon, weakly acidic resins, and strongly acidic macroreticular polymeric resins.

Without intending any limitation on the scope of the present invention and as merely illustrative, this invention is explained below in specific terms as applied to one specific embodiment of the invention, the continuous esterification of acetic acid by methanol to form methyl acetate and water using Amberlyst™-15, a strongly acidic macroreticular polymeric resin, to effect both the catalysis of the esterification in both the fixed catalyst bed and the simulated moving bed and to effect the separation of the products in the simulated moving bed. For ease of understanding, the simulated moving bed in the illustration described below is limited to having eight sub-beds housed in one chamber, however, other commonly-known configurations may be used. Also, while only one fixed catalyst bed is described in the illustration, multiple fixed catalyst beds connected in series may be used. The required apparatus is first described and then the process of the invention as applied to the embodiment is discussed.

Referring now to the apparatus as illustrated in the drawing, the first stage begins with line 16 which conducts a feed mixture of methanol and acetic acid to fixed catalyst bed 17 which houses an effective amount of the catalyst Amberlyst™-15. Line 12 conducts the effluent from fixed catalyst bed 17 to the second stage of the process with the effluent being a mixture of methanol, acetic acid, methyl acetate and water. In the second stage of the invention, distribution lines 1–8 are available to conduct liquid streams to or from the simulated moving bed 10. Simulated moving bed 10 houses eight sub-beds of Amberlyst™-15 which performs both the catalyst function and the adsorbent function. The distribution lines connect with the simulated moving bed at locations between successive sub-beds. The distribution lines 1–8 are also connected to a rotary valve 11. Rotary valve 11 is further connected to line 12 which conducts the effluent from the first stage fixed catalyst bed to the valve, line 13 which conducts raffinate, a mixture of methyl acetate diluted in methanol, away from the valve, line 14 which conducts desorbent, methanol, to the valve, and line 15 which conducts extract, water diluted in methanol, away from the valve. Each of the lines 12–15 is provided with a flow rate sensor and flow control valve (not shown). When necessary, lines 12 and 14 may also be equipped with a pump (not shown).

Using the described apparatus, the invention is performed as follows. The flow rates of each of the lines 12–15, and 16 and the step time of rotary valve 11 may be first set to selected values based on the operator's experience. The feed mixture containing a 1:1 molar mixture of methanol and acetic acid is introduced via line 16 to the fixed catalyst bed 17. As the methanol and acetic acid contact the Amberlyst-15 catalyst, the esterification reaction is catalyzed and methyl acetate and water are formed. Due to equilibrium limitations, however, the reaction will not go to completion and the effluent conducted in line 12 is a mixture of methyl acetate, water, methanol, and acetic acid. The effluent is conducted through line 12 to the second stage of the invention.

The starting position of rotary valve 11 in the second stage of the invention is not important; for this illustration the starting position of rotary valve 11 is such that the desorbent is directed to simulated moving bed 10 through distribution line 1, the extract is directed from simulated moving bed 10 through distribution line 3, the effluent from the first stage is directed to simulated moving bed 10 through distribution line 5, and the raffinate is directed from simulated moving bed 10 through distribution line 8. When the step time has elapsed, rotary valve 11 advances one index and now directs the desorbent through distribution line 2, the extract through distribution line 4, the effluent from the first stage through distribution line 6, and the raffinate through distribution line 1. When the step time has again elapsed, the streams will again be directed to the next successive distribution line in the direction of the flow, and the continued progression of the streams will simulate the movement of the solid bed in the countercurrent direction.

For ease of understanding, the operation is described with rotary valve 11 in the starting position as above. When the effluent from the first stage, conducted in distribution line 5, enters simulated moving bed 10 and contacts the Amberlyst™-15, the methyl acetate, which is weakly absorbed by the Amberlyst™-15, is carried with the fluid flow and withdrawn from the bed in the raffinate stream conducted in distribution line 8. The water, which is absorbed by the Amberlyst™-15, is carried with the solid bed in its countercurrent simulated movement thereby being separated from the effluent mixture. The water is desorbed from the Amberlyst™-15 by the desorbent, methanol, that is conducted to the bed through distribution line 1. The water is withdrawn from simulated moving bed 10 in the extract stream conducted in distribution line 3. The raffinate and the extract both contain methanol, and each stream may be treated downstream in a fractionator (not shown) to remove and recycle the methanol. An azeotrope may form between the methyl acetate and the methanol, and further treatment such as extractive distillation may be required. Since the product water is immediately removed from the effluent mixture, the equilibrium of the esterification reaction is shifted to favor additional product formation. The methanol and acetic acid, still being in contact with the catalyst, are then able to be catalytically esterified, and additional methyl acetate and water are formed. Again, the water is immediately adsorbed and removed, preserving the equilibrium shift to favor product formation, and the reaction continues.

It must be emphasized that the above description is merely illustrative of a preferred embodiment and is not intended as an undue limitation on the generally broad scope of the invention. Moreover, while the description is narrow in scope, one skilled in the art will understand how to extrapolate to the broader scope of the invention such as the application of the invention to additional reactions.

What is claimed is:

1. A two-stage continuous process for effecting a chemical reaction and concurrently separating at least one product formed in said chemical reaction comprising:

a. introducing one or more reactants to a fixed catalyst bed effective to catalyze the chemical reaction and form an effluent containing unconverted reactants and at least one product;

b. introducing, at different locations of a simulated moving bed, a desorbent and said effluent to said simulated moving bed containing a catalyst effective to catalyze said chemical reaction and an adsorbent to selectively adsorb at least one component of the effluent; and c. collecting at least one product-containing stream from the simulated moving bed.

2. The process of claim 1 where the reactants, products, and desorbent are in the liquid phase.

3. The process of claim 1 where the reactants, products, and desorbent are in the vapor phase.

4. The process of claim 1 where the desorbent is a material capable of desorbing the selectively adsorbed component.

5. The process of claim 4 where the desorbent is a reactant capable of desorbing the selectively adsorbed component.

6. The process of claim 1 where the catalyst in the fixed catalyst bed and the catalyst in the simulated moving bed are identical.

7. The process of claim 1 where the catalyst and adsorbent in the simulated moving bed are present in a ratio of from about 1:50 to about 50:1.

8. The process of claim 1 where the simulated moving bed contains a solid that is effective both as a catalyst and as an adsorbent.

9. The process of claim 1 where said reactants are an alcohol and a carboxylic acid and said products are an ester and water.

10. The process of claim 9 where the alcohol is methanol, the carboxylic acid is acetic acid, and the ester is methyl acetate.

11. The process of claim 1 further comprising a fluid carrier material present in a mixture with said reactants.

12. The process of claim 1 where said fixed catalyst bed comprises two or more serially connected fixed catalyst sub-beds.

13. The process of claim 1 further comprising where substantially all of at least one reactant is converted in the simulated moving bed.

14. A two-stage continuous process for effecting a chemical reaction and concurrently separating at least one product formed in said chemical reaction comprising:

a. introducing one or more reactants to a fixed catalyst bed effective to catalyze the chemical reaction and form an effluent containing an equilibrium mixture of unconverted reactants and at least one product;

b. introducing, at different locations of a simulated moving bed, a desorbent and said effluent to said simulated moving bed containing a catalyst effective to catalyze said chemical reaction and an adsorbent to selectively adsorb at least one component of the effluent; and c. collecting at least one product-containing stream from the simulated moving bed.

15. The process of claim 14 where the reactants, products, and desorbent are in the liquid phase.

16. The process of claim 14 where the reactants, products, and desorbent are in the vapor phase.

17. The process of claim 14 where the desorbent is a material capable of desorbing the selectively adsorbed component.

18. The process of claim 17 where the desorbent is a reactant capable of desorbing the selectively adsorbed component.

19. The process of claim 14 where the catalyst in the fixed catalyst bed and the catalyst in the simulated moving bed are identical.

20. The process of claim 14 where the catalyst and adsorbent in the simulated moving bed are present in a ratio of from about 1:50 to about 50:1.

21. The process of claim 14 where the simulated moving bed contains a solid that is effective both as a catalyst and as an adsorbent.

22. The process of claim 14 where said reactants are an alcohol and a carboxylic acid and said products are an ester and water.

23. The process of claim 22 where the alcohol is methanol, the carboxylic acid is acetic acid, and the ester is methyl acetate.

24. The process of claim 14 further comprising a fluid carrier material present in a mixture with said reactants.

25. The process of claim 14 where said fixed catalyst bed comprises two or more serially connected fixed catalyst sub-beds.

26. The process of claim 14 further comprising where substantially all of at least one reactant is converted in the simulated moving bed.

* * * * *